United States Patent [19]

Chun et al.

[11] 3,948,991

[45] Apr. 6, 1976

[54] CYCLIC ALDOL CONDENSATION PROCESS AND CATALYST REGENERATION PROCEDURE

[75] Inventors: Sun W. Chun, Murrysville; Franklin E. Massoth, Valencia; Howard G. McIlvried, McCandless Township, Allegheny County, all of Pa.

[73] Assignee: Gulf Research & Development Company, Pittsburgh, Pa.

[22] Filed: Apr. 21, 1972

[21] Appl. No.: 246,267

Related U.S. Application Data

[63] Continuation-in-part of Ser. No. 837,912, June 30, 1969, abandoned.

[52] U.S. Cl. ...... 260/586 E; 260/590 E; 260/593 R; 260/598; 260/599; 260/601 H; 260/601 R; 260/602; 260/632 R
[51] Int. Cl.² ............ C07C 47/36; C07C 47/50; C07C 49/06; C07C 49/42

[58] Field of Search ........ 260/601 R, 598, 599, 632, 260/593, 586 E, 590 E, 602; 252/411, 454

[56] References Cited

UNITED STATES PATENTS

| | | | |
|---|---|---|---|
| 1,999,388 | 4/1935 | Bader et al. | 252/411 R X |
| 2,317,494 | 4/1943 | Thomas | 252/411 R X |
| 2,479,999 | 8/1949 | Clark | 252/411 R X |
| 3,238,120 | 3/1966 | Sale | 252/411 R X |
| 3,542,878 | 11/1970 | Swift | 260/601 R |

*Primary Examiner*—Richard J. Gallagher
*Assistant Examiner*—D. B. Springer

[57] ABSTRACT

A cyclic aldol condensation process in which a silica-supported metallic tin catalyst is contacted in sequence with a carbonyl compound at an elevated temperature and with hydrogen for regeneration at a higher temperature.

4 Claims, No Drawings

CYCLIC ALDOL CONDENSATION PROCESS AND CATALYST REGENERATION PROCEDURE

This application is a continuation-in-part of Ser. No. 837,912, filed June 30, 1969, now abandoned.

The present invention relates to a process for the aldol condensation of carbonyl compounds in which the carbonyl compounds are contacted with a silica-supported metallic tin catalyst at an elevated temperature and the catalyst is regenerated in hydrogen at a higher temperature. More particularly, the invention relates to a process for the regeneration of a coke deactivated silica supported metallic tin catalyst by treating the deactivated catalyst in hydrogen at an elevated temperature.

As used herein, carbonyl compounds mean aldehydes and ketones. These carbonyl compounds are condensed in the presence of a catalyst at an elevated temperature. For example, acetaldehyde condenses to 2-butenal, acetone condenses to mesityl oxide, n-butyraldehyde condenses to 2-ethyl-2hexenal and the like. When a supported metallic catalyst is used for this catalyzed reaction, it will ordinarily become deactivated over a period of time as the result of the deposition on the catalyst of carbonaceous deposits or coke. For example, when metallic tin is used as the catalyst for the aldol condensation of carbonyl compounds at an elevated temperature as described in U.S. Pat. No. 3,542,878, the tin becomes substantially deactivated over a period of time either partly or primarily as a result of carbonaceous deposits or coke. Deactivation can also, in part, result from the partial oxidation of active tin metal to inactive tin oxide by oxygen contained in the carbonyl compound feed stream. According to this patent, the deactivated tin catalyst is regenerated by burning off the carbonaceous deposits in air at an elevated temperature and then in a second stage the burned-off catalyst is reduced to metallic tin in a hydrogen atmosphere.

We have unexpectedly discovered that this expensive and time consuming two-state procedure recommended heretofore for regenerating a metallic tin on silica catalyst can be supplanted by a simple and economical one-stage regeneration process. In our invention the deactivated metallic tin on silica catalyst is regenerated in one step to substantially original activity for the aldol condensation reaction by the hydrogen treatment of the deactivated catalyst at an elevated temperature without the use of an oxygen-containing gas treatment. It is unexpected that this one-step hydrogenation procedure would completely regenerate the carbon coated catalyst because it is well known that silica possesses very low hydrogenation activity. The hydrogenation procedure therefore would not be expected to remove sufficient carbon from the silica-supported catalyst to regenerate the catalyst to useful activity. We have discovered as expected, from the low hydrogenation activity of silica, that the deactivated metallic tin on silica catalyst, which has been treated by the one-step hydrogenation process of our invention, contains a significant amount of carbon after full hydrogenation, that is, between about five and about 10 percent carbon, but surprisingly we have discovered that the regenerated catalyst possesses its original activity despite the high carbon content.

The surprising discovery that the tin on silica catalyst, is regenerated to substantially its original activity despite its high carbon content of at least about 5 percent carbon is in shart contrast with petroleum hydrocarbon cracking catalysts which are generally deactivated and spent when they contain from 1 to 3 percent coke and must be regenerated to contain 0.5 percent coke or less. Thus, it is very unexpected that the regenerated catalyst of the instant invention contains between about 5 and about 10 percent carbon and yet is regenerated to substantially its original activity particularly in view of the fact that deactivated cracking catalysts contain less coke than the carbon content of the fully regenerated catalysts of the present invention. It is further surprising that the fully regenerated catalyst possesses the same life before regeneration is required as the freshly prepared catalyst despite the high initial carbon content of the regenerated catalyst. As used herein in connection with the silica supported metallic tin catalyst, the expression "deactivated" or "substantially deactivated" means that the catalyst contains more than about 10 percent carbonaceous deposits determined as elemental carbon.

In carrying out the aldol condensation process a vaporized stream of the carbonyl compound undergoing condensation is admixed with hydrogen and the mixed gas stream is passed through the reactor in contact with the metallic tin catalyst to carry out the condensation reaction. This reaction will continue for a significant period of time; however, the catalyst gradually collects carbonaceous deposits and the tin may gradually oxidize to tin oxide with a loss in its activity and at some point in time it must be regenerated. This is readily accomplished in a cyclic process by stopping the input of the carbonyl compound while continuing the flow of the hydrogen gas at a higher temperature. This hydrogen treatment at the elevated temperature is continued for a suitable period of time until the catalyst has been regenerated to substantially its original activity. Even though this treatment in hydrogen removes carbonaceous deposits and converts tin oxide to metallic tin, there is still a substantial amount of these carbonaceous deposits remaining on the catalyst after the catalyst has been regenerated to substantially its original activity by our procedure, that is, carbonaceous deposits containing between about 5 and about 10 percent elemental carbon remain on the catalyst. Surprisingly, these deposits remaining after the hydrogen-reactivation treatment do not interfere with the activity of the catalyst for the aldol condensation reaction. The expressions "coke" and "carbonaceous deposits" are used interchangeably herein, while "carbon" generally refers to elemental carbon.

The process can be used to condense a wide variety of aldehyde, ketone and mixed carbonyl feeds and is general for those carbonyl compounds which are known in the art to be capable of undergoing condensation. Carbonyl compounds containing from two to 20 carbon atoms are particularly desirable for condensation according to our process, however, even higher molecular weight carbonyl compounds can be used. At least one of the carbonyl compounds in the feed to our process must contain an alpha hydrogen atom.

The carbonyl compound can be of the general formula:

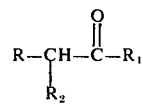

where R, $R_1$ and $R_2$ can be the same or different and each is selected from the group consisting of hydrogen, alkyl of one to 18 carbon atoms, alkylene of two to six carbon atoms, aryl of six to 10 carbon atoms, aralkyl of seven to eight carbon atoms, or where $R_1$ and $R_2$ can be joined together to form a five or six carbon saturated or mono-saturated ring structure and mono- or dichloro derivatives thereof.

Among carbonyl compounds having an available alpha hydrogen atom which may be used as the feed either alone or admixed with one or more other carbonyl compounds are acetaldehyde, propionaldehyde, n-butylraldehyde, isobutyradehyde, n-valeraldehyde, isovaleraldehyde, n-capronaldehyde, n-caprylaldehyde, n-caprinaldehyde, n-lauralaldehyde, n-tridecanal, n-palmitaldehyde, n-stearaldehyde, n-eicosyladehyde, $\beta$-ethylcapronaldehyde, $\beta$-hexenylaldehyde, cyclohexylacetaldehyde, cyclohexenylacetaldehyde, $\beta$-cyclohexylpropionaldehyde, phenylacetaldehyde, p-tolylacetaldehyde, xylyacetaldehyde, formylacetaldehyde, etc. Also included in this group of carbonyl compounds which can be used as a reactant in our process are acetone, methylethylketone, methylisobutylketone, methylisoamylketone, methyl n-hexylketone, methyl n-decylketone, cyclohexanone, cyclohexenone, cyclopentanone, cyclopentenone, and the like. Additionally, carbonyl compounds without an alpha hydrogen atom, such as formaldehyde, dimethyl propanal, benzaldehyde, chloral, phosgene, glyoxal, etc., may be condensed with at least about 50 mol percent of carbonyl compounds containing at least one alpha hydrogen atom. Thus formaldehyde and acetaldehyde form acrolein after dehydration, while benzaldehyde forms cinnamaldehyde with acetaldehyde after dehydration, and glyoxal and acetaldehyde form 2-buten-1,4-diol as a main product after dehydration.

The metallic tin catalyst is desirably supported on a high surface area support, in general the higher the surface area the greater the activity of the finished catalyst. Thus, although a surface area of about 10 $M^2/g$. provides catalytic activity, it is preferred that the catalyst have a final surface area of at least 50 $M^2/g$. in order to obtain sufficient activity for commercial advantage. Supports containing a surface area of at least 100 $M^2/g$. are more preferred while those containing at least 250 $M^2/g$. are the most preferred for this condensation reaction. The support is non-acidic silica and does not contain substantial impurities, such as alumina, to cause it to become acidic in character. Non-acidic silica is used as the support in order to minimize or substantially eliminate undesired by-products which would result from an acidic support such as a silica-alumina support. The silica support can be prepared from silica gel, sodium treated silica gel, kieselguhr, and the like. The tin can be incorporated on the support either before or after it has been calcined. Catalysts containing from about one up to about 75 weight percent, preferably up to about 40 weight percent, tin metal will catalyze the condensation reaction. Better yields of the condensed product are obtained with catalysts containing from about five to 20 weight percent tin, and the best yields result with catalysts containing from about 10 to 15 weight percent tin.

The catalyst can be produced by precipitating a tin compound onto a solid silica support of high surface area, or by impregnating the support with a tin compound, drying and calcining the support containing the tin compound to produce tin oxide and reducing the tin oxide to metallic tin at an elevated temperature. Any tin compound which is soluble in the treating solution, preferably water, can be used for the impregnating solution, such as stannic chloride, stannic bromide, organotin compounds, such as stannous acetate, stannous oxalate, dicyclopentadienyl tin (II), etc. When stannous chloride is added to water, it forms a finely dispersed white precipitate, probably $Sn(OH)Cl\cdot XH_2O$, which is absorbed by the support, such as silica gel. When tin metal is added to aqueous nitric acid, a white dispersion, probably the double salt $SnO\cdot Sn(NO_3)_2$, is formed which is also suitable for impregnation of the support. A suitable organic solvent, such as dimethylformamide or dimethylsulfoxide can be used in the treating solution for the organotin compounds.

Any suitable reducing gas can be used to reduce the tin oxide to metallic tin. Hydrogen gas is the preferred reductant either used alone or in combination with one or more reducing gases or inert gases. The lower paraffins are also useful herein. The temperature of reduction is not critical. Since the reduction involves a time-temperature relationship, the temperature must be sufficiently high and the time sufficiently long to obtain substantial reduction to the tin metal. For example, it has been ascertained that reduction of tin oxide, $SnO_2$, on silica gel for six hours at 700° F. results in substantially complete reduction to metallic tin to the beta form while it only takes 4 hours at 930° F. for the equivalent result, both of these reductions taking place with hydrogen passing over the catalyst at a gas hourly space velocity of 150 to 200. Reduction of the tin oxide to metallic tin can take place at a temperature as low as about 500° F. provided that the reduction time is sufficiently long. The resulting reduced catalyst is metallic tin in the beta form, as identified by X-ray diffraction analysis on the high surface area silica support.

The temperature at which the condensation reaction is conducted falls within the broad range of about 225° to about 575° F. with the preferred temperature range being about 400° F. to about 550° F. At the lower temperatures the reaction speed is slow while too high a temperature is avoided to prevent undesired side reactions. The reactions, furthermore, is conducted at a temperature at which the reactant and product are stable. For example, acetaldehyde begins to decompose at about 480° F. The pressure used in the reaction may be from subatmospheric to about 300 p.s.i.g. The preferred pressure is atmospheric pressure. Since the aldol condensation reaction taking place is a vapor-phase reaction, the temperature and pressure are selected and correlated with the boiling point of the carbonyl compound undergoing condensation in order to insure that the feed is in the vapor-phase at reaction conditions.

A diluent is not necessary but is preferred to promote the reaction. The preferred diluent is hydrogen since it permits a simple cyclic operation to be carried out as described herein. The inert paraffins such as methane and ethane as well as nitrogen and helium are also suitable diluent gases. Hydrogen is also preferred because it will assist in maintaining the catalyst in the reduced state. However, the hydrogen may not be completely successful in this regard. Since the carbonyl compound contains oxygen in its structure, it is not possible to exclude all oxygen from the system. We have found that by some not completely understood reaction, the feed may slowly oxidize the metallic tin to inactive tin oxide. This gradual loss of beta tin together with the deposition of carbonaceous deposits results in a continuous decline in catalyst activity. When a diluent gas is used, it is used in a ratio of up to about 100 mols per mol of carbonyl compound and more preferably in the range of about 0.25 to about 10 mols per mol of carbonyl compound.

When the activity of the catalyst has decreased to a level at which regeneration is determined to be desirable, that is, when the catalyst contains more than about 10 percent carbon in the carbonaceous deposits or more advantageously at least about 20 percent carbon, the feed of the carbonyl compound to the reactor is stopped and hydrogen gas is passed over the catalyst at a higher temperature. In a cyclic process hydrogen gas is conveniently used as the diluent gas with the feed of carbonyl compound stopped and hydrogen gas continued for regeneration. The temperature is then raised to a temperature of at least about 650° F. and preferably a temperature between about 700° and 800° F. and the hydrogen gas is passed through the catalyst bed until the catalyst is regenerated. The temperature should not be so high as to cause a substantial degradation of the catalyst and can suitably be as high as about 1,000° F. The increase in temperature is accomplished by heating the hydrogen gas or the catalyst bed or both. The time required for regeneration can be from about 15 minutes to about 8 hours depending on the condition of the catalyst, the degree of deactivation, the temperature of regeneration, and the like. The catalyst regenerated in accordance with the invention to substantially its original activity for the aldol condensation reaction retains deposits containing between about 5 and about 10 percent elemental carbon.

If hydrogen is not used as the diluent for the feed carbonyl compound, a separate stream of heated hydrogen gas can be passed through the reactor for the regeneration cycle. The hydrogen stream is desirably at least about 50 percent hydrogen with the remainder constituting an inert gas or another reducing gas and preferably at least about 90 percent hydrogen. Although the hydrogen flow rate through the catalyst bed is not critical, a gas hourly space velocity of between about 500 to about 1500 is convenient for the regeneration procedure.

We now describe by way of specific examples the use of our invention, however, these examples are not to be construed in any manner as limiting our invention.

EXAMPLE 1

Twenty grams of stannous chloride, $SnCl_2 \cdot 2H_2O$, was added to 100 cc. of water with stirring. The resulting finely divided white dispersion was completely absorbed by 100 grams of a commercial grade silica gel to the point of incipient wetness. The impregnated silica gel was air-dried in an oven at 250° F. for 16 hours and then calcined at 940° F. for 20 hours. The resulting tin oxide on the silica gel was reduced to tin metal in a stream of hydrogen gas at 940° F. for 6 hours. The resulting catalyst analyzed 6.64 percent tin with a BET surface area of 284 $M^2/g$. The tin was identified as $\beta$-tin by X-ray diffraction analysis. It was gray in color and was free of any coke or carbon.

EXAMPLE 2

Catalyst prepared in Example 1 was placed in an externally heated stainless steel reactor, 48 inches long and having an ID of 1 inch. Reactant n-butyraldehyde was vaporized in a flash zone before being carried over the catalyst in a stream of heated hydrogen at a hydrogen to n-butyraldehyde molar ratio of about two and a temperature of 450° F. The n-butyraldehyde in the gas mixture was passed over the catalyst at a liquid hourly space velocity of one, and the hydrogen at a gas hourly space velocity of 500. The reaction was carried out at a pressure of 150 p.s.i.g.

During initial operation, the reaction showed about 71 percent conversion with a selectivity to 2-ethyl-2-hexenal of 90 percent. As the reaction was continued, the conversion decreased. At the end of 15 days of operation the conversion had decreased to 25 percent and regeneration was considered to be desirable. The input of the feed gas stream was stopped and a sample of the catalyst was removed for analysis. The hydrogen flow was then renewed at a gas hourly space velocity of 500 and its temperature was raised to 940° F. This regeneration of the catalyst was continued for 6 hours. At this point, hydrogen flow was stopped and another sample of catalyst was removed for analysis. Table I presents inspections for the fresh, aged and regenerated catalysts.

Table I

| Catalyst | Fresh | Aged | Regenerated |
|---|---|---|---|
| Color | gray | brown | black |
| Carbon, wt.% | 0 | 31.7 | 7.15 |
| BET area, $M^2/g$ | 284 | 104 | 294 |
| State of tin | $\beta$-tin | $\beta$-tin+$SnO_2$ | $\beta$-tin |

The regeneration procedure described restored the catalyst to an activity essentially the same as the fresh catalyst, surprisingly at a higher surface area and with a carbon content greater than 5 percent.

EXAMPLE 3

In a further experiment similar to Example 2, an n-butyraldehyde and hydrogen gas mixture at a hydrogen to n-butyraldehyde molar ratio of nine was passed over the catalyst at a temperature of 420° F., 15 p.s.i.g. pressure and a liquid hourly space velocity of n-butyraldehyde of 0.5. After 16 days of operation, the aged catalyst was reactived in hydrogen at 750° F. for 2 hours to the same activity as the fresh catalyst. Table II sets out the data on the fresh, aged and regenerated catalysts.

Table II

| Catalyst | Fresh | Aged | Regenerated |
|---|---|---|---|
| Color | gray | gray | black |
| Carbon,wt.% | 0 | 12.86 | 6.60 |
| BET area, $M^2/g$. | 284 | 238 | 250 |
| State of tin | $\beta$-tin | $\beta$-tin | $\beta$-tin |

EXAMPLE 4

A fresh batch of the catalyst of Example 1 was loaded into the reactor. The n-butyraldehyde was passed over the catalyst at a liquid hourly space velocity of 0.5 and a hydrogen gas hourly space velocity of 2,000 and at a temperature of 420° F. and a pressure of 15 p.s.i.g.

After 7 days on stream, the conversion had dropped from 54 to 46 percent. At this point the n-butyraldehyde feed was stopped and the catalyst was regenerated with hydrogen at the same conditions as used in Example 2. After regeneration, n-butyraldehyde feed was again introduced into the reactor and the condensation reaction was continued with the regenerated catalyst at the same operating conditions as used before the regeneration. Table III compares the conversion and selectivity to 2-ethyl-2-hexenal of the fresh and the regenerated catalyst and demonstrates that they are identical within experimental error.

Table III

| Days on Stream | Conversion | | Selectivity | |
| --- | --- | --- | --- | --- |
| | Fresh | Regenerated | Fresh | Regenerated |
| 1 | 54 | 52 | 95 | 93.5 |
| 2 | 49 | 48 | 96 | 96.5 |
| 3 | 49 | 45 | 95.5 | 96.5 |
| 4 | 46 | — | 95.5 | — |
| 5 | — | 46 | — | 97.5 |
| 6 | 45 | 44 | 96.5 | 95.5 |
| 7 | 46 | 44 | 96 | — |

Additional runs demonstrated an identical result, that is, that the tin metal on silica catalyst can be regenerated to its original activity by regeneration in hydrogen without the traditional intervening oxidation step despite high residual carbon content. Furthermore, it has been demonstrated that the life of the regenerated catalyst, that is, the period of time that it can be used before it becomes deactivated to a state at which regeneration is required, is substantially identical with the life of the fresh catalyst. This is particularly surprising because the regenerated catalyst starts with a substantial amount of carbon remaining, that is, between about 5 and about 10 percent carbon, after the regeneration procedure.

In addition to the specific reactions described above the following reactions are illustrative: n-capryaldehyde condenses to 2-hexyl-2-decanal; n-lauralaldehyde condenses to 2-decyl-2-tetradecenal; n-eicosylaldehyde condenses to 2-octadecyl-2-docosenal; 3-butenal condenses to 2-vinyl-2,5-hexadienal; cyclopentanone condenses to 2-(1-cyclopentyl)cyclopentanone; 4-chlorobutyraldehyde condenses to 2-chloroethyl-6-chlorohexenal; methylphenylketone condenses to 1,3-diphenyl-2-buten-1-one; and methylcyclohexyl ketone condenses to 1,3-dicyclohexyl-2-buten-1-one. Furthermore, phenylacetaldehyde condenses to 2,4-diphenyl-2-butenal; cyclohexylacetaldehyde condenses to 2,4-dicyclohexyl-2-butenal; p-tolylacetaldehyde condenses to 2,4-di-p-tolyl-2-butenal; β-(2,4-dichlorophenyl)-propanol condenses to 2-(2,4-dichlorophenylmethyl)-5-(2,4-dichlorophenyl)-2-pentanal; etc.

It is to be understood that the above disclosure is by way of specific example and that numerous modifications and variations are available to those of ordinary skill in the art without departing from the true spirit and scope of the invention.

We claim:

1. In a cyclic process for the aldol-condensation of a carbonyl compound wherein the carbonyl compound is condensed by flowing it over a catalyst comprising metallic tin on a high surface area support consisting essentially of non-acidic silica until the activity of said catalyst is decreased by carbonaceous deposits and then reactivating the catalyst, the improvement which comprises the step of reactivating the deactivated catalyst when the carbon content of the carbonaceous deposits on the deactivated catalyst is greater than about 10 percent of the catalyst weight by stopping the feed of the carbonyl compound and flowing a stream of a reducing gas containing at least about 50 percent hydrogen with the remainder being an inert diluent gas in contact with said deactivated catalyst at conditions including a temperature of at least about 650° to about 1,000° F. to produce a reactivated catalyst with a carbon content of between about five percent and about 10 percent as carbonaceous deposits on the reactivated catalyst.

2. A process in accordance with claim 1 in which the carbon content of the carbonaceous deposits on the deactivated catalyst is at least about 20 percent carbon.

3. A process in accordance with claim 1 in which the temperature is between about 700° and about 800° F.

4. A process in accordance with claim 1 in which said reducing gas contains at least about 90 percent hydrogen.

* * * * *